US010632304B2

United States Patent
Muessig et al.

(10) Patent No.: US 10,632,304 B2
(45) Date of Patent: Apr. 28, 2020

(54) DELIVERY SYSTEMS FOR AN INTRAVASCULAR ELECTRODE LINE AND CORRESPONDING DELIVERY METHODS AND CATHETERS

(71) Applicant: BIOTRONIK SE & Co. KG, Berlin (DE)

(72) Inventors: Dirk Muessig, West Linn, OR (US); Andrew B. Kibler, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/439,243

(22) Filed: Feb. 22, 2017

(65) Prior Publication Data
US 2017/0259057 A1 Sep. 14, 2017

Related U.S. Application Data

(60) Provisional application No. 62/306,092, filed on Mar. 10, 2016.

(51) Int. Cl.
*A61N 1/05* (2006.01)
*A61N 1/36* (2006.01)
*A61F 2/82* (2013.01)
*A61N 1/372* (2006.01)
*A61N 1/375* (2006.01)
*A61F 2/95* (2013.01)

(52) U.S. Cl.
CPC ....... *A61N 1/0551* (2013.01); *A61N 1/36053* (2013.01); *A61F 2/82* (2013.01); *A61F 2/95* (2013.01); *A61N 1/3605* (2013.01); *A61N 1/372* (2013.01); *A61N 1/37516* (2017.08)

(58) Field of Classification Search
CPC .. A61N 1/0551; A61N 1/056; A61N 1/37053; A61N 1/36114; A61N 1/0558
See application file for complete search history.

(56) References Cited

U.S. PATENT DOCUMENTS

| | | | |
|---|---|---|---|
| 2011/0166482 | A1 | 7/2011 | Stack et al. |
| 2014/0128750 | A1 | 5/2014 | Ransbury et al. |
| 2016/0067474 | A1 | 3/2016 | Muessig et al. |

FOREIGN PATENT DOCUMENTS

| | | |
|---|---|---|
| EP | 2 495 012 A1 | 9/2012 |
| EP | 2 992 925 A1 | 3/2016 |

OTHER PUBLICATIONS

European Search Report and Annex to the European Search Report on European Patent Application No. EP 16 16 3110.6, dated Aug. 8, 2017 (7 pages).

*Primary Examiner* — Tammie K Marlen
(74) *Attorney, Agent, or Firm* — Buchanan Ingersoll & Rooney PC

(57) ABSTRACT

A catheter for delivering an implantable stimulation device in a patient, the catheter including a probe having a plurality of electrodes, wherein the probe is transferrable from a reduced delivery state for movement within a human body to an expanded tissue contacting state, in which at least one electrode of the plurality of electrodes is in contact with tissue; and at least one holder to which an implantable stimulation device is attachable, wherein the at least one holder is positioned proximally to the probe section by a predefined distance "d".

14 Claims, 4 Drawing Sheets

DELIVERY SYSTEMS FOR AN INTRAVASCULAR ELECTRODE LINE AND CORRESPONDING DELIVERY METHODS AND CATHETERS

CROSS-REFERENCE TO RELATED APPLICATIONS

This patent application claims the benefit of U.S. Provisional Patent Application No. 62/306,092, filed on Mar. 10, 2016, which is hereby incorporated by reference in its entirety.

TECHNICAL FIELD

The present invention refers to two alternative delivery systems for an implantable stimulation device, in particular, an intravascular electrode lead and corresponding delivery methods and catheters.

BACKGROUND

Neurostimulation is the therapeutic alteration of activity in the central, peripheral or autonomic nervous systems by means of implantable pulse generators and implanted stimulation devices. Neurostimulation may treat a variety of symptoms or conditions, for example, vagus nerve stimulation (VNS) is an adjunctive treatment for certain types of intractable epilepsy and treatment-resistant depression. A neurostimulator, which is a special kind of implantable pulse generator (IPG), is a battery powered device designed to deliver electrical stimulation to the brain, central and peripheral nervous systems.

The vascular system contains numerous locations within it and in contact with it which are electro-active and present the possibility of therapeutic electrical stimulation. One example of such a location is in the right brachiocephalic vein-Superior Vena Cava (SVC) junction by which runs the right vagus nerve. Stimulation of the vagus nerve has been shown to result in an anti-inflammatory effect and a reduction in sympathetic drive, which is beneficial to patients suffering from a variety of conditions including, but not limited to, heart failure, acute ischemic attack, and atrial and ventricular arrhythmias.

Trans-vascular stimulation electrodes, as one embodiment of implantable stimulation devices, exist for chronic application, for example, for phrenic nerve stimulation, however, most of them are designed for small vessels and cannot be used in large veins. Hence, a system capable of delivering or recording electric fields in a vessel near a neuroactive target location being compatible with large veins would be advantageous.

Trans-vascular stimulation of the vagus nerve has been demonstrated previously with basket catheters. One problem with common expandable basket-style stimulation catheters is that they are designed for acute stimulation and are not appropriate for chronic stimulation.

In a proposed implantable (neuro-)stimulation device, electrodes are positioned intravascularly within a blood vessel (for example, a jugular vein, superior vena cava, or inferior vena cava) and are used to transvascularly stimulate nervous targets located outside the vasculature. For maintaining the electrodes in contact with the blood vessel wall, anchors have been developed. Such anchors include structural features that allow the anchor to radially engage a vessel wall. The anchor may include a band, sleeve, mesh or other framework formed of shape memory materials (for example, nitinol or shape memory polymer) or other non-biodegradable materials like, for example, stainless steel.

One or more of the drawbacks of the state of art (surgical dissection to gain nerve access) may be avoided or at least reduced by use of an implantable (neuro-)stimulation device in the implementation of an intravascular electrode lead which has been developed by the inventors and is subject of the U.S. patent application Ser. No. 14/814,096, which is incorporated in this application in its entirety by reference. Said intravascular electrode lead comprises an electrode shaft; a plurality of filaments being made of a conductive, non-biodegradable material, running in longitudinal direction within the electrode shaft and protruding distally beyond a distal end of the electrode shaft, each filament terminating in at least one electrode element; and a support member being arranged distally from the distal end of the electrode shaft and being dilatable from a compressed state to an radially expanded state, wherein the support member is attached to the filaments and made of a biodegradable material.

The support member may be a radially expandable framework of struts. For example, the support member may have a stent-like or graft stent-like design (also called "stent"). The biodegradable stent is constructed as a support member with inter-woven or mechanically affixed conductive, non-biodegradable filaments. The filaments may be connected to an electrically conducting, biologically compatible tether.

Said intravascular electrode lead relies on a support member, which allows primary fixation and biological encapsulation as a secondary fixation mechanism. The support member, once it is deployed and expanded at the implantation site, and—if equipped with a biodegradable support member—until the support member is completely dissolved, cannot be retracted or explanted.

The nerve bundles that this implantable (neuro-)stimulation device targets have natural physiological variability with respect to their location around the vasculature and cannot be seen via standard medical imaging methods. Thus, it is necessary to ensure that the vascular location of deployment of the known intravascular electrode lead is therapeutically appropriate prior to deployment. In addition, after location of the desired site of deployment, the act of delivery and deployment must not introduce significant stress to the vasculature or uncertainty in the final site of deployment.

Existing solutions for delivery of stents are known. These include balloon-inflatable catheters, where the delivery catheter is comprised of a catheter which includes a lumen along its length, terminating at its distal end in a balloon. A stent rides on this balloon until it reaches the desired delivery location, and the balloon is inflated with liquid via liquid injection into the catheter lumen. In addition, electrically active catheters are known for the purpose of mapping electrical activity in the atria, and for delivering high frequency stimulation for ablation in the atria and renal system. However, there exists no delivery system and corresponding delivery method for the above mentioned intravascular electrode lead, i.e., none of the existing solutions for stent delivery allows for electrical probing of a target location before stent delivery, and none allows for precise delivery of the intravascular electrode lead to the desired vascular location found via probing.

Thus, there is a need for a delivery tool which allows a physician to locate an optimal endovascular neuromodulation location and accurately deliver a neuromodulation stent-based electrode to this location.

The present invention is directed toward overcoming one or more of the above-identified problems.

SUMMARY

In order to address the mentioned delivery needs, a catheter for delivering an implantable stimulation device in a patient is provided which comprises a probe comprising a plurality of (probe) electrodes. The probe of this catheter is transferrable from a reduced delivery state for movement within a human body—which may be a vessel—to an expanded tissue contacting state, in which at least one electrode of the plurality of electrodes is in contact with tissue. Further, the catheter comprises at least one holder to which an intravascular stimulation device is attachable. The catheter may be steerable via suitable means like, for example, a guidewire, a mandrel or pull wires to easily reach the desired implantation location.

The plurality of electrodes of the catheter may be located at or on the probe and is/are configured to physically contact the tissue. Further, the plurality of electrodes may be attached to, or plated on, or embedded in, or integrated in the probe.

In a first embodiment, the probe of the catheter comprises at least one expandable centering element, configured to contact the tissue, when it is transferred to the tissue contacting state. The at least one expandable centering element may be selected from the group of inflatable balloons, expandable baskets, spring-loaded metallic mesh, spring-loaded polymer mesh or combinations thereof.

In a second alternative embodiment, the probe of said catheter comprises at least one expandable helical section configured to contact the tissue, when it is transferred to the tissue contacting state. Preferably, the expandable helical section has a winding of at least 360°. The at least one expandable helical section has a reduced delivery state, in which it has an elongate shape. If the at least one expandable helical section is in the tissue contacting state, it has a radially expanded helical shape, which is suitable to contact body tissue.

In each of both embodiments, the plurality of electrodes is situated at or on the probe, i.e., in the first mentioned embodiment at or on the at least one expandable centering element or embedded in the outer surface of the at least one expandable centering element, preferably distributed circumferentially and longitudinally over the expandable centering element, or in the second embodiment at or on the helical section or embedded in the outer surface of the helical section.

In case of the second embodiment comprising the at least one expandable helical section, the plurality of electrodes is chosen from the group consisting of ring electrodes, point contact electrodes, micro needle contact electrodes and combinations thereof. If the probe comprises at least one expandable centering element, the electrodes may be chosen from the group of point contact electrodes, square formed or longitudinal formed electrode elements, micro needle contact electrodes and combinations thereof. Furthermore, associated to at least one electrode of the plurality of electrodes, other components may be associated like, for example, thermal elements (e.g., thermistors), drug eluting reservoirs, micro injection needles for injection of suitable drugs supporting, for example, evoking of nerve potentials.

Further, the plurality of electrodes and—if applicable—the components of the first embodiment comprising at least one expandable centering element, may be attached, formed, implemented or integrated on a Printed Circuit Board element (PCB), whose material is highly flexible. One example for such a PCB material is Liquid Crystal Polymer (LCP), which is attached or adhered onto the expandable centering element.

The catheter of both disclosed embodiments may further comprise an elongated catheter shaft having a proximal end and a distal end, and wherein the probe is located at or near the distal end. Preferably, the probe is more flexible than the shaft.

For delivering and implantation of the implantable stimulation device, the holder is positioned proximally to the probe by a predefined distance. This predefined distance allows an exact placement of the holder, after localizing the suitable implantation site. Preferably, the holder is a dilatable balloon.

The present invention further provides a delivery system comprising a catheter according to the mentioned invention, and at least one implantable stimulation device, wherein the at least one implantable stimulation device is attached to the at least one holder. The implantable stimulation device comprises at least one support member being dilatable from a compressed state to a radially expanded state, and at least one electrode contact element. Preferably, the implantable stimulation device is an implantable electrode lead comprising at least one support member and an elongate electrode shaft, said support member being arranged distally from the distal end of the electrode shaft. Further, the at least one support member may be detachably attached to the at least one holder.

The implantable stimulation device may comprise a plurality of filaments being made of a conductive, non-biodegradable material, running in longitudinal direction within the electrode shaft and protruding distally beyond a distal end of the electrode shaft, each filament terminating in at least one electrode contact element on or at the support member. Furthermore, the support member may be made of a biodegradable material.

Also, the implantable stimulation device may be an intravascular electrode lead.

The present invention further provides a corresponding method for delivering of an implantable stimulation device. The method includes the steps of: (a) providing a catheter for delivering an implantable stimulation device in a patient comprising a probe, which comprises a plurality of electrodes, wherein the probe is transferrable from a reduced delivery state for movement within a human body to an expanded tissue contacting state, in which at least one electrode of the plurality of electrodes is in contact with tissue, and at least one holder to which an implantable stimulation device may be attachable; (b) transferring the probe from said reduced delivery state to said expanded tissue contacting state; and (c) stimulating the tissue via the at least one electrode of the plurality of electrodes, which are in direct contact with the tissue and/or sensing activation of the stimulation target.

In case of missing or low activation of the stimulation target, the method further comprises the step of transferring the probe from said expanded tissue contacting state to said reduced delivery state, and rearranging/moving the probe within the body by translation and/or rotation of the catheter, and repeating steps (b) and (c) until sensing sufficient activation of the stimulation target.

In case of sufficient activation of the stimulation target, the method further comprises the step of transferring the probe from the expanded tissue contacting state to the reduced delivery state and moving the catheter within the body such that the holder bearing the implantable stimulation device is positioned at the stimulation target, which is identified with step (c), and dilating the at least one support member of the implantable stimulation device from a compressed state to a radially expanded state, in which the support is fixedly attached to the tissue.

In particular, in the first mentioned embodiment of the present invention, a delivery system for an intravascular electrode lead of an intravascular neurostimulation device is provided. The delivery system of the first alternative includes an intravascular electrode lead comprising an electrode shaft and a support member being arranged distally from the distal end of the electrode shaft and being dilatable from a compressed state to a radially expanded state. Further, a catheter is comprised, which is comprising of an expandable centering element, for example, in form of an inflatable probe balloon, positioned at a distal end of the catheter, the inflatable probe balloon including arrangement plurality of probe electrodes at or on or embedded in its outer surface; and a holder in form of an inflatable support member delivery balloon positioned proximally to the inflatable probe balloon, wherein the support member of the intravascular electrode lead is positioned on the inflatable delivery balloon.

The present invention further provides a catheter used in the delivery system according to the first alternative, which is a separable part of the delivery system.

Moreover, there is provided a corresponding method of delivering an intravascular electrode lead using the delivery system according to the first embodiment. The method includes the steps of: (a) providing a delivery system according to the first embodiment; (b) inflating the inflatable probe balloon at a vessel location from a reduced delivery state to an expanded tissue contacting state such that at least one electrode of the plurality of probe electrodes is in contact with an endovascular surface; and (c) stimulating the endovascular surface via the at least one electrode of the plurality of probe electrodes, which are in direct contact with the tissue, and/or sensing activation of the stimulation target.

In case of missing or low activation of the stimulation target, the method further comprises the step of deflating the inflatable probe balloon from the expanded tissue contacting state to the reduced delivery state, rearranging/moving the inflatable probe balloon within the vessel by translation and/or rotation of the catheter, and repeating steps (b) and (c) until sensing sufficient activation of the stimulation target.

In case of sufficient activation of the stimulation target, the method further comprises the step of deflating the inflatable probe balloon and translating the catheter within the vessel such that the inflatable delivery balloon bearing the intravascular electrode lead is positioned at the stimulation target, which is identified with step (c), and inflating the inflatable support member delivery balloon to expand the support member of the intravascular electrode lead.

In other words, this embodiment of the present invention may also disclose a multi-lumen delivery catheter with a proximal end and a distal end for delivering an intravascular electrode lead, which can be attached to a vessel location. The distal end comprises an inflatable probe balloon, which may be flexible, and proximal to the inflatable probe balloon by a predefined distance, a support member delivery balloon. The proximal end of the catheter may comprise a port for inflating the support member delivery balloon, port(s) for adjusting the inflatable probe balloon, and connector(s) for electrically connecting the plurality of probe electrodes. The delivery catheter may preferably also contain a distally capped central lumen to allow a guide wire to be fed inside to manipulate its curvature.

The catheter for delivering an implantable stimulation device may include a proximal indicator which allows the operator to slide the catheter by the predefined distance in order to accurately place the support member of the intravascular electrode lead at a vascular location probed by the inflatable probe balloon immediately prior. In other words, the catheter preferably contains a longitudinal mark provided at a proximal end of the catheter having the same length as a distance d between the geometric centers of the inflatable probe balloon and the support member delivery balloon. The intravascular electrode lead is mounted to the inflatable balloon of the catheter at a distance from the inflatable probe balloon, preferably the predetermined distance is 1 to 6 cm.

The vessels targeted by the intravascular electrode lead are intended to be sufficiently large in diameter to support a stent-based fixation mechanism, and the delivery system described before. Being of a large diameter, the targeted vessels also support a degree of longitudinal translation of any implanting device. The disclosed delivery system takes advantage of this allowance by utilizing a translation of the catheter for delivering an intravascular electrode lead along the vessel to position the therapeutic intravascular electrode lead at a therapeutically responsive site determined via stimulation from the distal end of the delivery tool.

The delivery system, respectively a catheter according to the first alternative embodiment, thus includes an expandable centering element, designed as inflatable probe balloon studded with an arrangement of a plurality of probe electrodes at or on or embedded in its outer surface, at least one electrode of these plurality of probe electrodes contact the vessel wall upon inflation to test the location for therapeutic response. This balloon may be deflated and translated or rotated to a new position for testing. A lumen in the catheter allows inflation and deflation of the probe balloon independently from the support member delivery balloon/holder.

Preferably, said probe balloon contains a plurality of probe electrodes in a limited angular location and aligned with a rotation mark visible (with fluoroscopic imagery) on a proximal end of the catheter for delivering an implantable stimulation device, respectively, the delivery system, which can be rotated to probe the vessel wall radially. The goal of limiting the angular stimulation field of the flexible electrical probe is to limit the number of conductors required to fit in the catheter, and optimize therapy energy delivery. In such an arrangement, the therapeutic intravascular electrode lead will also have a radially limited stimulation zone which is aligned with the radially limited stimulation zone of the flexible electrical probe (which is built by the arrangement of the plurality of electrodes) such that a longitudinal translation of the delivery system in the distal direction causes the stimulation zone of the therapeutic intravascular electrode lead to align with the targeted vascular location last probed by the flexible electrical probe. A lumen in the delivery catheter is connected with this support member delivery balloon and a proximal port which allows the support member delivery balloon to be expanded/dilated to place the therapeutic intravascular electrode lead.

In particular, in the second alternative embodiment, a delivery system for an intravascular electrode lead of an intravascular neurostimulation device is provided. The delivery system of the second alternative includes an intravascular electrode lead comprising an electrode shaft and a support member being arranged distally from the distal end of the electrode shaft and being dilatable from a compressed state to a radially expanded state. Further, a catheter is comprised, which is comprising of an expandable helical section arranged at a distal end of the catheter; and a holder in form of an inflatable delivery balloon positioned proximally to the expandable helical section, wherein the support member of the intravascular electrode lead is positioned on the inflatable delivery balloon.

Again, the present invention also provides a catheter used in the delivery system according to the second alternative, which is a separable part of the delivery system.

Moreover, there is provided a corresponding method of delivering an intravascular electrode lead of an intravascular neurostimulation device using the delivery system according to the second embodiment. The method includes the steps of: (a) providing a delivery system according to the second embodiment; (b) expanding the expandable helical section at the distal end of the catheter from a reduced delivery state to an expanded tissue contacting state towards a vessel location such that at least one electrode of the plurality of probe electrodes is in contact with an endovascular surface of the vessel; and (c) stimulation of the endovascular surface via the at least one electrode of the plurality of probe electrodes, which are in direct contact with the tissue, and/or sensing activation of the stimulation target.

In case of missing or low activation of the stimulation target, the method further comprises the step of transferring the expandable helical section to the delivery state and rearranging the expandable helical section within the vessel by translation and/or rotation of the catheter, and repeating steps (b) and (c) until sensing sufficient activation of the stimulation target.

In case of sufficient activation of the stimulation target, the method further comprises the steps of reducing the expandable helical section to the delivery state and translating the catheter within the vessel such that the inflatable support member delivery balloon bearing the intravascular electrode lead is positioned at the stimulation target, which is identified with step (c); and inflating the inflatable delivery balloon as to expand the support member of the intravascular electrode lead.

Hence, the delivery system according to the second embodiment basically departs from the delivery system according to the first embodiment in that the inflatable probe balloon is replaced by an expandable helical section at the distal end of the catheter. Said expandable helical section may have a specific contour supporting the location of the electrodes during moving or rearranging the catheter within the vessel. The contour may be, for example, a 'pig-tail' design as illustrated in the Figures.

In summary, using the catheter, the delivery systems and corresponding delivery methods allows for precise delivery of the implantable stimulation device to a targeted and verified body tissue. Together, these inventions allow for minimally invasive, explantable neuromodulation therapy for the treatment of hypertension, heart failure, and a variety of neuropathically mediated illnesses. Preclinical tests have demonstrated the feasibility of endovascular stimulation of the vagus nerve. Endovascular stimulation delivery allows reduced surgical procedure complexity, reduced patient scarring, and neurostimulator delivery via surgical methods familiar to electrophysiologists, enabling a product delivery well suited to the target market.

Further embodiments of the present invention could be learned from the following description, in combination with the Figures, and/or the dependent claims.

DESCRIPTION OF THE DRAWINGS

These and other aspects and advantages of the present invention will become apparent and more readily appreciated from the following descriptions taken in conjunction with the drawings in which.

DETAILED DESCRIPTION

Figure 1:
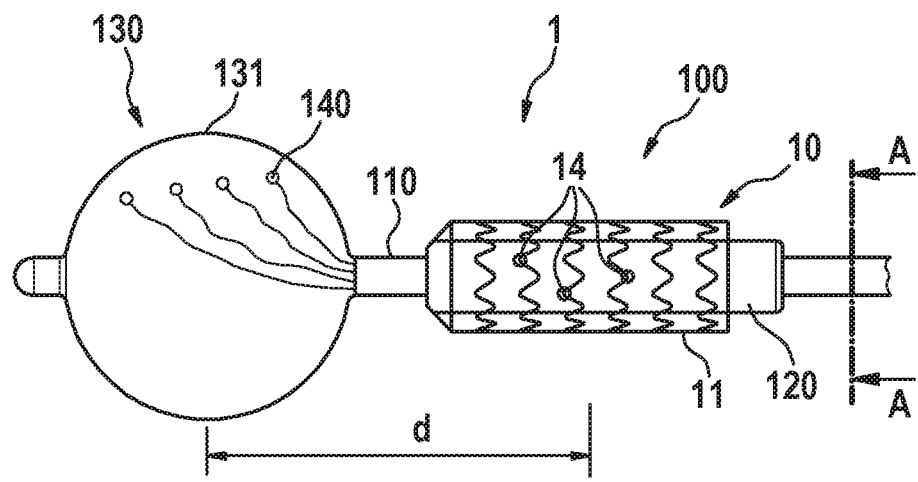
FIG. 1 shows the distal end of a catheter of a delivery system according to a first embodiment of the present invention.

Reference will be made in detail to embodiments of the present invention. The embodiments described herein are explanatory, illustrative, and used to generally understand the present disclosure. The same or similar elements and the elements having same or similar functions are denoted by like reference numerals throughout the descriptions.

FIG. 1 shows the distal end of a catheter 100, which is part of a delivery system 1 according to a first embodiment of the present invention. The delivery system 1 is used for delivering an implantable stimulation device 10. In this embodiment, the implantable stimulation device 10 is designed as an intravascular electrode lead of an implantable medical device, like an intravascular neurostimulation device, at a specific location of a vessel. The intravascular electrode lead 10, or more specifically the support member 11 thereof, is crimped on a holder 120, which in one embodiment is an inflatable support member delivery balloon. Furthermore, the catheter 100 comprises a probe 130, which comprises an inflatable probe balloon 131 positioned at the distal end of a catheter shaft 110. In this illustration, the probe balloon 131 is shown in an inflated state (expanded tissue contacting state). The inflatable probe balloon 131 includes a plurality of probe electrodes 140 on its outer surface, which are electrically connected via flexible electrode leads 113, shown in FIG. 6.

Here, the inflatable probe balloon 131 contains a plurality probe electrodes 140 in a limited angular location visible with fluoroscopic imaging and aligned with a rotation mark 150 visible on the distal end of the catheter 100 (see FIG. 6), which can be rotated to probe the vessel wall radially. The goal of limiting the angular stimulation field of the plurality of probe electrodes 140 is to limit the number of conductors required to fit in the catheter shaft 110, and optimize therapy energy delivery. In such an arrangement, the therapeutic intravascular electrode lead 10 may also have a radially limited stimulation zone which is aligned with the radially limited stimulation zone of the plurality of probe electrodes 140 such that a longitudinal translation of the delivery system 1 in the distal direction causes the stimulation zone to align with the targeted vascular location last probed by the probe 130. In alternative, the plurality of probe electrodes 140 on the surface of the inflatable probe balloon 131 may be similar to the arrangement of electrically active areas of the intravascular electrode lead 10 in the expanded stage of the support member 11.

A distance between the geometric center of the inflatable probe balloon 131 and the inflatable support member delivery balloon 120 may be, for example, up to 6 cm, and preferably 4 cm.

Figure 2:
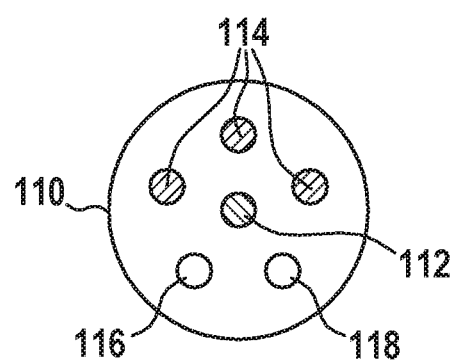
FIG. 2 shows a cross-section view through lead A-A of the catheter illustrated in FIG. 1.

FIG. 2 shows a cross-section view through line A-A of the catheter 100 illustrated in FIG. 1. A guide wire is provided in a central lumen 112 of the catheter 100 and—according to the exemplary embodiment—three lumens 114 are provided for accepting the plurality of filaments 113 for connecting the plurality of probe electrodes 140. Furthermore, the catheter shaft includes a lumen 116 connected to the inflatable probe balloon 131 and a lumen 118 connected to the delivery balloon 120.

Figure 3:
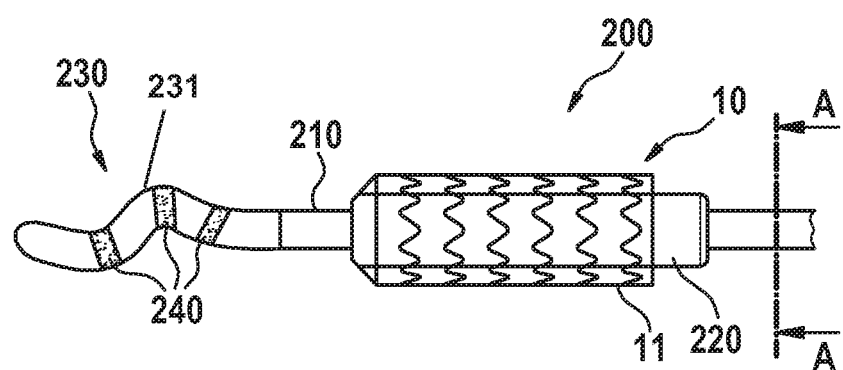
FIG. 3 shows the distal end of a catheter of a delivery system according to a second embodiment of the present invention.
Figure 4:
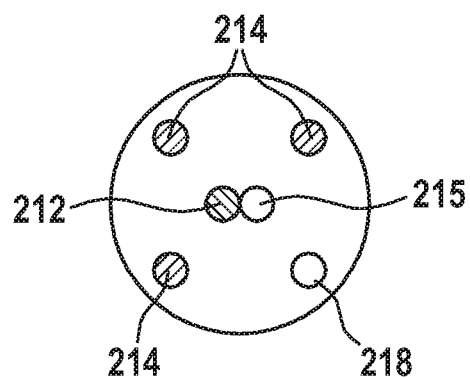
FIG. 4 shows a cross-section view through lead A-A of the catheter illustrated in FIG. 3.
Figure 6:
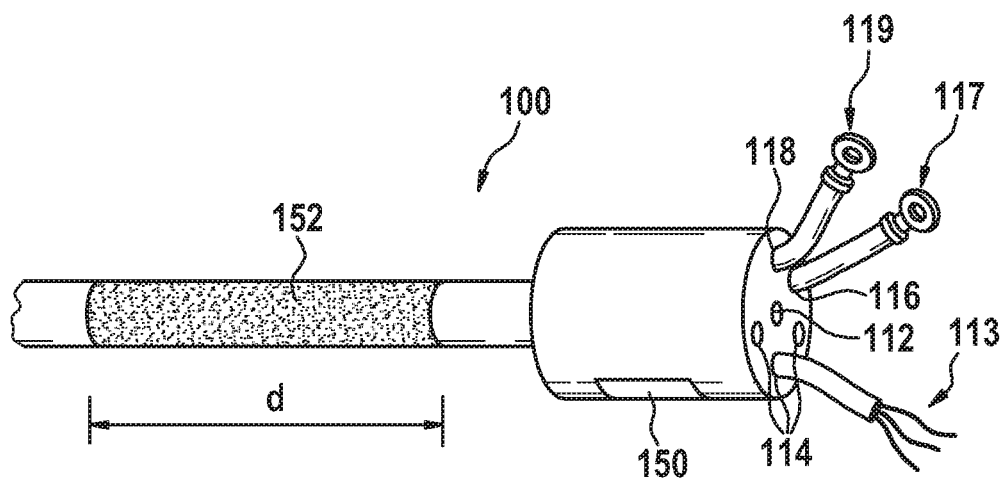
FIG. 6 shows an embodiment of the proximal end of a delivery system, exemplarily illustrated based on the first embodiment.

FIG. 6 exemplarily illustrates an embodiment of the proximal end of the catheter 100. The lumens 116 and 118 do bear balloon inflation Luers 117 and 119; Luer 117 for inflating the inflatable probe balloon 131 and Luer 119 for inflating the inflatable delivery balloon 120. There is further an electrode orientation mark 150 on the proximal end of the catheter 100 so as to control rotation of the probe 130, respectively, delivery balloon 120. A longitudinal mark 152 has the same length as the distance "d" between the inflatable probe balloon 131 and the delivery balloon 120 and could be used for controlling a translation of the delivery balloon 120 towards the former position of the probe balloon 131. Although this embodiment is illustrated based on the use of catheter 100 with an inflatable probe balloon 131, the nearly identical proximal end of a delivery system 2 may be used with a catheter 200 with a probe 230 comprising at least one expandable helical section 231 as illustrated in FIGS. 3 and 4 and which will be described later in this document.

In the following, a corresponding method of delivering the intravascular electrode lead 10 will be explained in more detail. The method includes the steps of:

(a) providing the before mentioned delivery system 1 of the first embodiment and advancing it to an endovascular location within a vessel;

(b) inflating the inflatable probe balloon 131 at a vessel location from a reduced delivery state to an expanded tissue contacting state such that at least one electrode of the plurality of probe electrodes 140 is in contact with an endovascular surface of the vessel;

(c) stimulating the endovascular surface via the at least one electrode of plurality of probe electrodes 140 and sensing activation of the stimulation target;

in case of missing or low activation of the stimulation target, deflating and rearranging the inflatable probe balloon 131 from the expanded tissue contacting state to the reduced delivery state, rearranging/moving the inflatable probe balloon within the vessel by translation and/or rotation of the catheter 100; and repeating the steps (b) and (c) mentioned above until sensing sufficient activation of the stimulation target.

in case of sufficient activation of the stimulation target, deflating the inflatable probe balloon 131 and translating the catheter 100 within the vessel such that the inflatable delivery balloon 120 bearing the intravascular electrode lead 10 is positioned at the stimulation target, which is identified with step (c); and inflating the inflatable delivery balloon 120 as to expand the support member 11 of the intravascular electrode lead 10.

Figure 5:
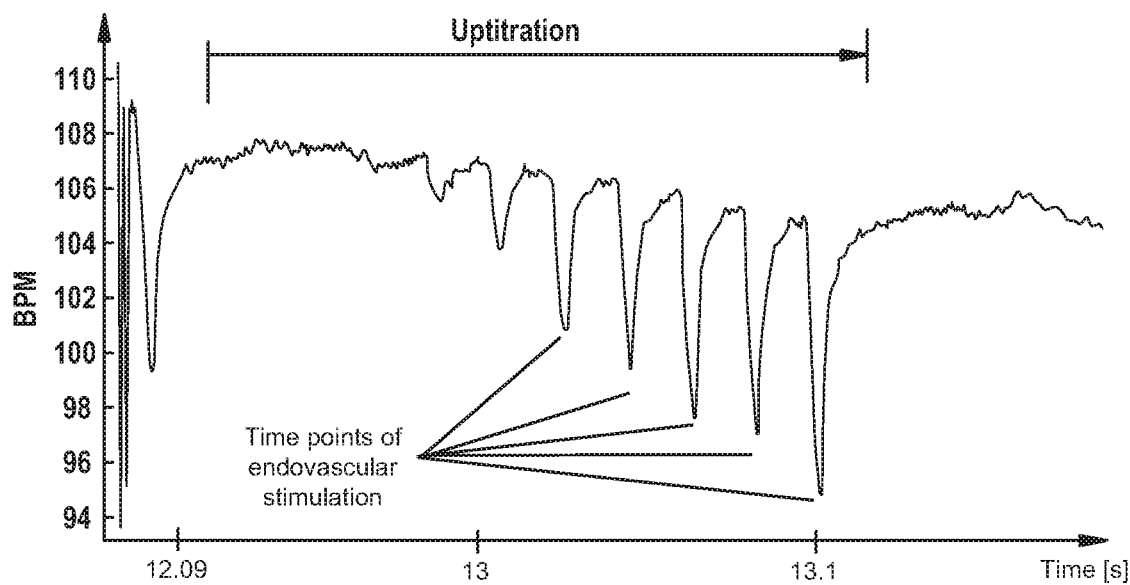
FIG. 5 shows experimental results demonstrating the vagal parasympathetic activation from endovascular stimulation.

FIG. 5 illustrates one possible way to find suitable stimulation targets by stimulating the tissue and sensing the vagal parasympathetic activation during endovascular stimulation of step (c). At least one possibility is uptitration of stimulation pulses until a level, at which sensed results meet a predetermined criteria, which could be a decreased heart rate. In the example of FIG. 5, a clear vago-parasympathetic response of the stimulation could be found. In such case, the probe balloon 131 will be deflated and the delivery balloon 120 according to the embodiment of FIGS. 1, 2 and 6 will be transferred into the same position by translation of distance "d" (for example, 4 cm) without any rotation. Then, the delivery balloon 120 is inflated and thereby the support member 11 of the intravascular electrode lead 10 is dilated and attached to the vessel.

In summary, in the first embodiment a delivery systeml comprising a catheter 100 with at least two expandable centering element is disclosed—a distal probe 130 with a first expandable centering element 131 containing stimulation electrodes on its surface, and a proximal second expandable centering element 120 which carries and deploys the electrode lead 10. At least one electrode of the plurality of probe electrodes 140 on the first expandable centering element 131 is brought into contact with the vascular surface when the first endovascular location is reached. Stimulation is provided to the endovascular surface via this plurality of probe electrodes 140, and activation or lack of activation of the stimulation target is confirmed. The first expandable centering element 131 is then collapsed and the catheter re-positioned multiple times if necessary to locate the desired implantation location exhibiting the desired response to stimulation. Once the optimal site of stimulation is located, the first expandable centering element 131 is collapsed a final time and the delivery system is advanced a known, fixed distance equal to the distance "d" from the first expandable centering element 131 on the catheter 100 to the second expandable centering element 120 on the catheter 100. The second expandable centering element 120 is then expanded to deploy the electrode lead 10 to the target stimulation location.

FIG. 3 shows the distal end of a catheter 200 of a delivery system 2 according to a second embodiment of the present invention. Same features do have the same reference signs as in the delivery system 100 according to the first embodiment illustrated in FIGS. 1, 2 and 6. The second embodiment comprises a catheter 200 comprising a catheter shaft 210 and proximal to the distal end of the catheter shaft 210 a holder 220 in form of an inflatable support member delivery balloon. The second embodiment departs from the first embodiment basically in that the probe balloon 131 is replaced by a probe 230 comprising at least one expandable helical section 231 at the distal end of a catheter shaft 210 of the catheter 200. The expandable helical section 231 includes a plurality of probe electrodes 240. Here, at the distal end of the catheter shaft 210 a probe 230 is attached, which comprises, in this second embodiment, at least one expandable helical section 231, which simplifies the use of the catheter 200 during the measurement of vascular response. In a relaxed state, the probe 230 has an elongated form and extends along the longitudinal axis of the catheter shaft 210. In the expanded helical position, to which the expandable helical section 231 is brought for contacting the endovascular surface of the vessel during stimulating and sensing, said expandable helical section 231 has a helical shape, which coils around an imaginary elongation of the longitudinal axis of the catheter shaft 110. Preferably, the expandable helical section 231 has a winding of at least 360° around the imaginary longitudinal axis.

FIG. 4 shows a cross-section view through line A-A of the catheter shaft 210 illustrated in FIG. 3. Again, there are lumens 214 for accepting the plurality of filaments 113 for connecting the plurality of probe electrodes. Furthermore, the catheter shaft 210 includes a lumen 218 connected to the delivery balloon 220. A lumen 215 is designed for acceptance of a tension cable or tension wire for expanding the expandable helical section 231 of the probe 230. The lumen 215 extends through the catheter shaft 210 into the attached expandable helical section 231 and runs within the probe 230 in a helical manner around a real longitudinal axis of the helical section 231.

In the following, a corresponding method of delivering the intravascular electrode lead 10 will be explained in more detail. The method includes the steps of:

(a) providing the before mentioned delivery system 2 of the second embodiment and advancing it to an endovascular location within a vessel;

(b) expanding the expandable helical section 231 at the distal end of the catheter shaft 210 from a reduced delivery state to an expanded tissue contacting state towards a vessel location such that at least one electrode of the plurality of probe electrodes 240 is in contact with an endovascular surface of the vessel;

(c) stimulating the endovascular surface via at least one electrode of the plurality of probe electrodes 240 and sensing activation of the stimulation target;

in case of missing or low activation of the stimulation target, reducing the expandable helical section 231 to the delivery state and rearranging the expandable helical section 231 within the vessel by translating and/or rotating the catheter 210, and repeating steps (b) and (c) until sensing sufficient activation of the stimulation target;

in case of sufficient activation of the stimulation target, reducing the expandable helical section 231 to the delivery state and translating the catheter 200 within the vessel such that the inflatable support member delivery balloon 120 bearing the intravascular electrode lead 10 is positioned at the stimulation target, which is identified with step (c); and inflating the inflatable support member delivery balloon 120 as to expand the support member 11 of the intravascular electrode lead 10.

Figure 7:
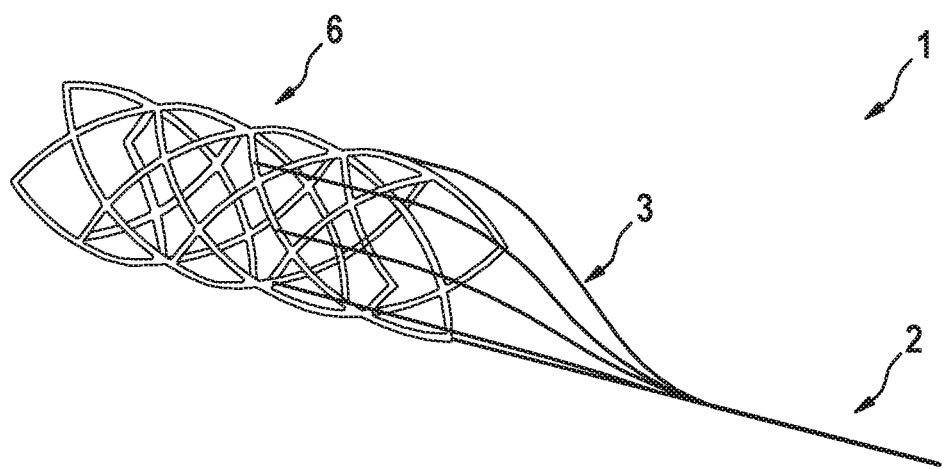
FIG. 7 shows an example of an electrode lead for transvascular stimulation of nerve tissue.

FIG. 7 illustrates an example of an implantable stimulation device 10 designed as implantable electrode lead for intravascular stimulation of nerve tissue. As can be seen, the electrode lead 10 in this embodiment is formed as an intravascular electrode lead and has an elongate electrode shaft 12 formed as an elongate tube with at least one filament 13, which runs fixedly attached in longitudinal direction within the electrode shaft. The shaft 12 has the shape and material of a commonly known cardiac electrode lead. A support member 11 that could be dilated from a compressed to a radially expanded state is arranged distally from the distal end of the elongate shaft 12 and is temporarily attached to the electrode shaft by the at least one filament 13, which protrudes distally beyond the distal end of the electrode shaft. Further, each filament 13 is terminating in at least one electrode element 14, situated on or at the support member 11. The proximal end of this electrode lead 10 can be electrically coupled to a medical implant like an implantable pacemaker, an implantable defibrillator or an IPG like an implantable nerve stimulator (intravascular neurostimulation device). Therefore, the proximal end is carried out like a commonly known implantable electrode lead with a plug coupled to the shaft and electrical contacts, which are electrically connected to the filaments 13.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS 1, 2 delivery system
10 implantable stimulation device
11 support member
12 electrode shaft
13 filament(s)
14 electrode element
100, 200 catheter
110, 210 catheter shaft
112, 212 central lumen
113 electrode wires, connected to electrodes 140, 240
114, 214 lumen designed for accepting electrode wires 113
116 lumen connected to the expandable centering element 130
117 Luer for inflating the probe balloon 130
118, 218 lumen connected to the holder 120
119 Luer for inflating the inflatable delivery balloon 120
110, 210 catheter shaft
120, 220 holder
130, 230 probe
131 expandable centering element
140, 240 plurality of (probe) electrodes
150 electrode orientation mark
152 longitudinal mark
215 lumen designed for acceptance of a tension cable
231 expandable helical section

We claim:

1. A delivery system comprising:
an implantable stimulation device; and
a catheter for delivering the implantable stimulation device in a patient, the catheter comprising:
a probe comprising a plurality of electrodes, wherein the probe is transferrable from a reduced delivery state for movement within a human body to an expanded tissue contacting state, in which at least one electrode of the plurality of electrodes is in contact with tissue; and
at least one holder,
wherein the at least one holder is positioned proximally to the probe section by a predefined, fixed distance "d",
wherein the implantable stimulation device is detachably attached to the at least one holder, and
wherein the probe comprises at least one expandable helical section configured to contact the tissue, when the probe is transferred to the tissue contacting state.

2. The delivery system according to claim 1, wherein the plurality of electrodes is located at or on the probe and is configured to physically contact the tissue.

3. The delivery system according to claim 1, wherein the plurality of electrodes is attached to, or plated on, or embedded in, or integrated in the probe.

4. The delivery system according to claim 1, wherein the probe comprises at least one expandable centering element, configured to contact the tissue, when the probe is transferred to the tissue contacting state.

5. The delivery system according to claim 4, wherein the plurality of electrodes is situated at or on the at least one expandable centering element, and is distributed circumferentially and longitudinally over the expandable centering element.

6. The delivery system according to claim 4, wherein the at least one expandable centering element is selected from the group of inflatable balloons, expandable baskets, spring-loaded metallic mesh, spring-loaded polymer mesh or combinations thereof.

7. The delivery system according to claim 1, wherein the expandable helical section has a winding of at least 360°.

8. The delivery system according to claim 7, wherein the plurality of electrodes is chosen from the group consisting of ring electrodes, point contact electrodes and combinations thereof.

9. The delivery system according to claim 1, wherein the plurality of electrodes is situated at or on the helical section.

10. The delivery system according to claim 1, wherein the catheter further comprises a catheter shaft having a proximal end and a distal end, and wherein the probe is located at or near the distal end.

11. The delivery system according to claim 1, wherein the at least one holder is a dilatable balloon.

12. The delivery system according to claim 1, wherein the implantable stimulation device comprises at least one support member being dilatable from a compressed state to a radially expanded state, and at least one electrode contact element.

13. The delivery system of claim 12, wherein the implantable stimulation device is an implantable electrode lead comprising at least one support member and an elongate electrode shaft, said at least one support member being arranged distally from a distal end of the electrode shaft.

14. The delivery system of claim 12, wherein the at least one support member is detachably attached to the at least one holder.

* * * * *